United States Patent [19]
Gueret

[11] Patent Number: 5,211,892
[45] Date of Patent: May 18, 1993

[54] PROCESS FOR THE COMPACTION OF A POWDER MIXTURE PROVIDING AN ABSORBENT OR PARTIALLY FRIABLE COMPACT PRODUCT AND THE PRODUCT OBTAINED BY THIS PROCESS

[75] Inventor: Jean-Louis H. Gueret, Paris, France

[73] Assignee: L'Oreal, Paris, France

[21] Appl. No.: 733,181

[22] Filed: Jul. 19, 1991

[30] Foreign Application Priority Data

Jul. 20, 1990 [FR] France .................. 90 09327

[51] Int. Cl.⁵ .............................. B29C 43/02
[52] U.S. Cl. ..................... 204/23; 264/113; 264/123
[58] Field of Search ............... 264/23, 113, 123

[56] References Cited

U.S. PATENT DOCUMENTS

| | | | |
|---|---|---|---|
| 3,717,427 | 2/1973 | Bodine | 264/23 |
| 4,014,965 | 3/1977 | Stube et al. | 264/23 |
| 4,487,728 | 12/1984 | Hagen et al. | 264/23 |
| 4,548,771 | 10/1985 | Senapati et al. | 264/23 |
| 4,597,922 | 7/1986 | Durbin | 264/26 |
| 4,887,409 | 12/1989 | Israel et al. | 264/113 |
| 4,943,400 | 7/1990 | Hirano et al. | 264/113 |
| 4,957,668 | 9/1990 | Plackard et al. | 264/23 |

FOREIGN PATENT DOCUMENTS

| | | |
|---|---|---|
| 3437989 | 4/1986 | Fed. Rep. of Germany . |
| 2109838 | 5/1972 | France . |
| 58-81119 | 5/1983 | Japan .................. 264/23 |
| 61-181630 | 8/1986 | Japan .................. 264/23 |
| 877528 | 9/1961 | United Kingdom . |

OTHER PUBLICATIONS

Patent Abstracts of Japan, vol. 7, No. 95 (M-209) [1240], Apr. 21, 1983, p. 99.

*Primary Examiner*—Mary Lynn Theisen
*Attorney, Agent, or Firm*—Cushman, Darby & Cushman

[57] ABSTRACT

A new process for manufacturing pharmaceutical or cosmetic compacted powders providing an absorbent or partially friable compacted product, in which a quantity of powder mixture is placed at the bottom of a chamber in which a piston is made to slide in order to exert a compaction pressure on the powder mixture, wherein the powder mixture contains from 5 to 80% by weight of at least one thermoplastic product having a particle size of between 5 and 500 μ, the remainder being composed of at least one non-thermoplastic product containing from 0.5 to 20% by weight of a binder and, that, whilst pressure is being applied, the powder mixture is subjected to ultrasonic force.

8 Claims, 1 Drawing Sheet

PROCESS FOR THE COMPACTION OF A POWDER MIXTURE PROVIDING AN ABSORBENT OR PARTIALLY FRIABLE COMPACT PRODUCT AND THE PRODUCT OBTAINED BY THIS PROCESS

BACKGROUND OF THE INVENTION

Field of the Invention

The present invention relates to a process for the compaction of a powder mixture providing an absorbent or partially friable compact product and to the compacted product thus obtained.

Summary of the Invention

It is known to compact powder products, for example pharmaceutical preparations, in order to provide compressed tablets or pills, or cosmetic preparations, or to provide "compacts" for face makeup (blusher, eyeshadow). To effect compaction, the powder mixture to be compacted is placed at the bottom of a chamber in which a piston or punch is made to slide so that it compressed the powder mixture to ensure cohesion of the grains of powder.

In the case of cosmetic preparations, compaction must allow subsequent disintegration by friction and, under those conditions, the compressed tablet obtained is extremely fragile, especially when it is of reduced thickness; it has therefore to be manufactured in a godet to enable handling after compression. The bottom of the compaction chamber therefore consists of a metal or plastic godet in which a compacted product, generally called a "compact", is manufactured; the "compact" obtained is then used in its godet.

Until now, it has not been known how to obtain a "compact" which is both sufficiently friable to allow the makeup to be taken up and sufficiently solid to allow it to be handled without a godet.

Moreover, it is known that compaction processes need to employ high pressures which vary depending on the powder to be compacted. In order to lower the pressure needed to effect compaction and to facilitate the cohesion of the grains of powder, a binder is normally added, the best known one being zinc stearate.

This invention has for its object a process which enables "compacts" to be prepared which are both friable and solid without the use of a godet and which allows lower compaction pressures to be employed.

This invention relates to a process for the compaction of a powder mixture which provides a compacted product which is absorbent or partially friable, in which a quantity of powder mixture is placed at the bottom of a chamber and in this chamber a piston is made to slide, exerting compaction pressure on the said powder mixture, characterized in that the powder mixture contains from 5 to 80% by weight of at least one thermoplastic product, the remainder being composed of at least one non-thermoplastic product and in that during the exertion of pressure the powder mixture is subjected to ultrasonic force.

In the above definition and throughout the text of this application, the term "product" employed means either one compound or a mixture of several different compounds.

DESCRIPTION OF THE INVENTION

It has been discovered that when compaction is performed under ultrasound, the presence of a thermoplastic product in the powder mixture allows the formation of an internal and/or external framework (which will be explained in more detail below), which hold the non-thermoplastic product and provides compacts which can absorb liquids, where the compacted non-thermoplastic product contains absorbent substances, or partially friable compacts. When the quantity of thermoplastic product is below 5% by weight, sufficient framework to hold the non-thermoplastic product is no longer formed and when the quantity of thermoplastic product is higher than 80% by weight, it is not possible to obtain a compacted product that is sufficiently absorbent or friable.

DESCRIPTION OF THE PREFERRED EMBODIMENTS

Figure 1:
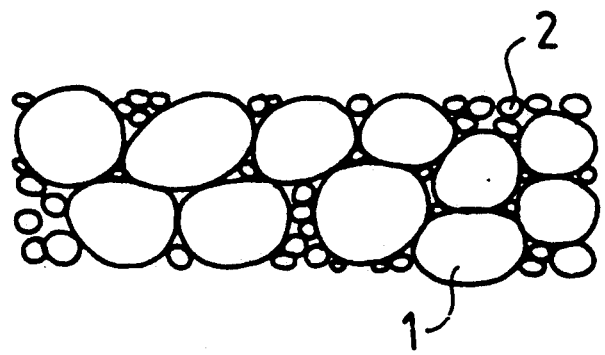
FIG. 1 shows in cross-section the structure of a non-impregnated absorbent compacted tablet obtained by the process described in example 1 where numeral 1 denotes the grains of thermoplastic product and numeral 2 denotes the grains of non-thermoplastic product.

Thermoplastic products which may be employed include polymers, copolymers or any mixture of polymers and/or copolymers having the property of being thermoplastic under operative conditions. Examples of thermoplastic polymers which may be employed according to the invention include polyethylene, polystyrene, polyamides, polyvinyl chloride and poly(ethylene terephthalate).

If a compacted perfumed product is desired, a perfumed polyethylene, such as that sold under the trade mark "Enka Fragrance Carriers" by Enka AG, may be employed.

The preferred thermoplastic product have a particle size, which may or may not be homogeneous, of between 5 and 500 $\mu$.

Non-thermoplastic products which may be employed include any mineral or organic substance or a mixture of these powder substances that are non-thermoplastic under operative conditions, which is capable of being compacted. Examples of minerals include talc, clays (in particular, kaolin), mica and mineral pigments such as titanium dioxide, zinc oxide or iron oxides. Examples of organic substances include powders of vegetable origin such as rice starch or silk powder, and non-thermoplastic polymer powders such as polyacrylates. The organic non-thermoplastic product may also consist of vegetable fibres or a mixture of vegetable fibres, for example cotton fibres.

The non-thermoplastic materials defined above may be coated in or impregnated with an impregnating fluid such as oil, a solvent, water, or a solution of an active substance in water or in a solvent. In this case, an absorbent, impregnated compact may be obtained immediately after compaction.

According to the invention, it is preferable to employ a non-thermoplastic material with a particle size, which may or may not be homogeneous, of from 2 to 200μ, This size range corresponding to the lengths of cut sections of fibres where the material is a fibre.

The non-thermoplastic product may contain from 0.5 to 20% by weight of a binder in order to facilitate the cohesion of the powder grains during compaction. The binder consists of wellknown products or a mixture of products, examples of which include zinc stearate, petrolatum, myristyl myristate and castor oil.

According to the invention, ultrasound is employed which will preferably have a frequency range of 10 to 100 kHz and on amplitude of from 20 to 60 μm; the power transmitted to the product during compaction will preferably be between 1 and 3 kW per $cm^3$ of compact. The duration of emission is generally between 0.25 s and 3 s; the duration taken generally increases with the thickness of the layer of mixture treated.

The pressure applied to the powder mixture during ultrasound emission is preferably between 40 and 200 bars. The piston employed to compress the powder mixture preferably consists of the sonotrode of an ultrasound generator.

It is known that the chamber in cross-section may be of various shapes (circular, oval, square or rectangular, which may or may not have rounded corners) and of various sizes, the surface of the piston in contact with the powder material having in cross-section the same shape and size, allowing for clearance to enable it to slide within the chamber. The bottom of the container and the surface of the piston in contact with the powder mixture may be flat; they may also, independently of each other, be of a non-flat shape, that is, for example, convex, with raised or hollow decorative motifs. Compacted products in the shape of a tile, dome or lozenge, in the form of a seal, or in other shapes may thus be obtained.

According to the different parameters of the process employed; pressure, ultrasonic power and frequency, duration of ultrasonic emission, nature and particle size of the thermoplastic and non-thermoplastic materials, different compacted products are obtained, that is to say, they are to a greater or lesser extent absorbent, friable, flexible or rigid.

The process of this application therefore provides a wide range of compacted products.

Moreover, it has been discovered, according to the invention, that the manner in which the different powder products are arranged in the compaction chamber has a considerable effect on the structure of the compacted product.

According to the first method of employing the invention, a layer of a homogeneous powder mixture is placed at the bottom of a compaction chamber; by "homogeneous mixture" is meant a mixture in which the various powder products are evenly distributed. In the compacted product obtained, the thermoplastic product forms a lattice which is evenly distributed throughout the mass, the said lattice holding the non-thermoplastic product within its meshes. In the case of a friable compacted product being desired, the compact obtained according to this process may allow up to 15% by weight of the powder that constitutes the compact to be removable.

According to the second method of employing the process of the invention, a powder mixture in the form of successive layers in which the proportions of thermoplastic and non-thermoplastic powders are different is placed at the bottom of the compaction chamber; it is preferable that the powder layer with the highest content of thermoplastic powder be placed at the bottom of the compaction chamber. More specifically, two layers are placed in the chamber: first a layer of thermoplastic product, then a layer of non-thermoplastic product possibly containing a small quantity, uniformly mixed, of homogeneous thermoplastic product.

Under these conditions, during the compaction process, the thermoplastic product placed at the bottom of the container partially rises up the side walls of the compaction chamber, while the greater part stays at the bottom of the chamber; there also occurs a slight penetration of the non-thermoplastic product into the layer of thermoplastic product and of the thermoplastic product into the layer of the non-thermoplastic product. The compacted product therefore comprises two zones: a zone mainly composed of the thermoplastic product, forming a sort of godet; and a zone within the said "godet" and composed mainly of the non-thermoplastic product. This second method of preparation is particularly advantageous where it is desired to prepare a partially friable compacted product, such as a cosmetic compact. It is in effect no longer necessary to perform a compaction in a godet, the godet being, as it were, formed "in situ" during compaction. In this case, the compact obtained may allow up to 70% by weight of the product subjected to compaction to be removable. This second method of preparation also has the advantages of enabling the preparation of very thin compacted products having a thickness of the order of one millimeter and which have no tendency to break during subsequent handling.

In accordance with the process of the invention, after compaction, the compacted product, when it is absorbent, may be filled by immersion in an impregnating fluid.

The present invention also has for its object the compacted product obtained by the process according to the invention, this product consisting of an absorbent or partially friable compact.

The compacted product may, according to the invention, be an absorbent product. In this case, it contains, as non-thermoplastic product, at least one absorbant material such as vegetable fibres, superabsorbent polymers, clays or their mixtures.

The absorbent compacted product may be in impregnable form or impregnated with a fluid which may or may not be volatile. In the latter case, impregnation may have been carried out either by employing microcapsules containing the impregnating fluid in the non-thermoplastic product or by immersing the compacted product in the impregnating fluid. Compacted products of varying rigidity, impregnated with sun oil, deodorant, stain remover or perfume, may thus be obtained. The user may employ the compacted product as an applicator of the impregnated product, similar to the way in which a soap is used. Where the impregnating fluid is a volatile material, the compact may be used to bring about the release of volatile material, which may be perfume, pesticide, disinfectant or other product, into a particular space.

The compact obtained may also be a partially friable product, particularly a compact for face makeup. This compacted product obtained from a layer of homogeous powder mixture is composed of an evenly distributed thermoplastic lattice holding the non-thermoplastic product may contain up to 15% by weight of friable product. The compact obtained may also be a partially friable product composed of two zones: a zone forming the godet which is mainly composed of thermoplastic product and a zone located inside the former zone which is mainly composed of non-thermoplastic product; such a compact is obtained by compacting a mixture in successive layers; in this case, the compact may contain up to 70% by weight of friable product. Such a compact may have a thickness in the region of a millimeter without risk of breakage during handling following compaction.

Compaction may also be performed directly on a support composed of a thermofusible material, allowing use of the compact. In this case, the support is designed to be equipped with a means of binding the compact to it. More specifically, compaction may be performed by the process according to the invention on a flocked rigid or flexible support; in this case, the pile of the flock is embedded in the compact after this has taken place and holds the compact on the support. If a makeup compact is thus produced, and compaction is limited to the central part of the flocked support, the support may be used to apply the makeup directly, the compact depositing on the skin the friable powder contained on the surface and the outer pile of the flocked support which is not covered by the compact enables the user to smooth evenly the powder makeup which has been deposited on the skin. Such a support may moreover consist of another flocked surface on the side that does not carry the compact which allows the user to finish smoothing the makeup evenly. The compaction support may also be provided by a sheet of a non-woven material containing of a phase of thermoplastic material such as a non-woven sheet composed of 70% by weight of cotton fibres and of 30% of polypropylene fibres.

The following examples, given as illustrative of and not limitative of the invention, will enable the invention to be better understood.

In all the following examples, a cylindrical compaction chamber was employed having a right circular section of 30 mm in diameter, in which was made to slide a cylindrical sonotrode of the same diameter, allowing for clearance, linked to an ultrasonic generator. The ultrasound had a frequency of 30 kHz; emission was at a power of 2 kW. The duration of emission was 2 s. The compaction pressure applied to the sonotrode was 100 bars: it was maintained for 2.5 s.

EXAMPLE 1

Preparation of a non-impregnated flat absorbent tablet

A layer of homogeneous powder mixture having the following composition (in % by weight) was placed at the bottom of a compaction chamber:

| | |
|---|---|
| Thermoplastic product: | |
| Polyamide sold under the trade name "Nylon 6.6" having a particle size of between 10 μm and 300 μm | 60% |
| Non-thermoplastic product: | |
| Cotton fibres (length: from 40μ to 1 mm) | 2% |
| Polyacrylate powder sold under the trade name "SUMIKAGEL" having a particle size of between 10 μm and 300 μm | 30% |
| Talc having a particle size of between 5 μm and 200 μm | 8% |

EXAMPLE 2

Preparation of an impregnated compacted tablet

The procedure was the same as in Example 1, but cotton fibres of 500 μm in length, impregnated with perfume in the proportion of 5% by weight of perfume in relation to the fibre weight, were employed. The superabsorbent was impregnated with an active principle composed of an aqueous alcoholic solution in the proportion of 300% by weight in relation to the weight of the superabsorbent. In formulating the composition of Example 1, whilst keeping the same proportions, the non-impregnated fibres and polyacrylate were replaced with the same components which were pre-impregnated.

The tablet contained after compaction may be used directly by application to the skin by the user.

EXAMPLE 3

Preparation of a rigid cosmetic powder compact

At the bottom of the chamber was placed a 5 cm layer of homogeneous powder mixture having the following composition (in % by weight):

| | |
|---|---|
| Thermoplastic product: | |
| Polyethylene wax, sold under the trade name "Akumist" by Allied Chemical, having a particle size of between 2 and 300 μm | 45% |
| Non-thermoplastic product: | |
| Pigmented silk powder caoted 5% by weight (in relation to the weight of non-coated silk powder) with a binder composed of myristyl myristate and having a particle size of 200 μm | 55% |

Figure 2:
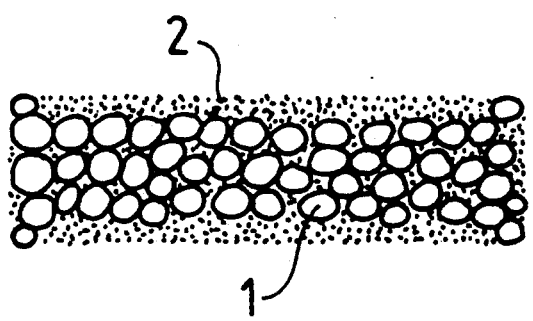
FIG. 2 shows in cross-section the structure of a rigid compacted tablet obtained by the process described in example 3 where numeral 1 denotes the grains of thermoplastic product and numeral 2 denotes the grains of non-thermoplastic product.

It was discovered that the structure of the compacted tablet obtained was that shown diagrammatically in FIG. 2, in which reference 1 indicates the grains of the thermoplastic product and reference 2 the grains of the non-thermoplastic product. The zone forming the godet was inside the compact and was demarcated by two surfaces of opposing concavity.

The tablet obtained was rigid; it could be used by rubbing with a brush, the powder thus taken up constituting at most 15% of the total weight of the tablet.

EXAMPLE 4

Preparation of a cosmetic powder compact composed of a flexible godet formed "in situ"

At the bottom of a compaction chamber was first placed a layer 5 mm thick of a thermoplastic product composed of a low density polyethylene powder, marketed under the trade-mark "Enka Fragrance Carrier" by Enka AG, then a layer 5 mm thick of a non-thermoplastic product composed of a pigmented silk powder coated 5% by eight (in relation to the weight of non-coated silk powder) with a binder composed of myristyl myristate. The polyethylene represented 15% by weight of the mixture and had a particle size of 50 μm. The coated powder had a particle size of 200 μm.

Figure 3:
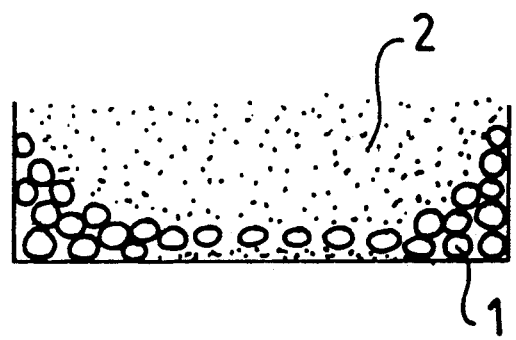
FIG. 3 shows in cross-section the structure of compacted cosmetic powder formed into a flexible godet obtained by the process described in example 4 wherein numeral 1 denotes the grains of thermoplastic product and numeral 2 denotes the grains of non-thermoplastic product.

After compaction, a tablet was obtained having the structure shown diagrammatically in FIG. 3, in which reference 1 indicates the grains of the thermoplastic product and reference 2 the grains of the non-thermoplastic product. The zone forming the godet was flexible and situated on the outside. The compact obtained was 2 mm thick and could be handled without breakage. It was discovered that approximately 50% by weight of the powder was friable when applied via a brush.

EXAMPLE 5

Preparation of an impregnated compacted tablet

At the bottom of the chamber was placed a layer of a homogeneous mixture having the following composition (in % by weight):

| Thermoplastic product | |
|---|---|
| Polyamide sold under the trade-name "Nylon 6.6" having a particle size of 70 $\mu$m | 50% |
| Non-thermoplastic product: | |
| Talc having a particle size of 150 $\mu$m | 45% |
| Perfume microcapsules containing a perfume and having a particle size of 80 $\mu$m | 5% |

Most of the microcapsules burst during compaction and the perfume impregnated the talc. The perfume was then released slowly into the atmosphere from the compacted tablet. The tablet obtained could be employed to perfume a space.

EXAMPLE 6

Preparation of a flexible cosmetic powder compact

Example 3 was repeated but the polyethylene wax sold under the trade-name "Akumist" was replaced with a low density polyethylene powder, sold by Enka under the trade-name "Accurel", the said powder being composed of microporous polymer particles.

It was discovered that the compacted tablet obtained was flexible and could be used by rubbing with a brush, the powder thus taken up constituting up to approximately 10% of the total weight of the tablet.

EXAMPLE 7

Preparation of a non-impregnated flat absorbent tablet

A compacted tablet as described in Example 1 was prepared by simply replacing the polyamide sold under the trade-name "Nylon 6.6" with the same quantity of low density polyethylene powder, sold under the trade-name "Accurel" and already employed in Example 6. An absorbent tablet was obtained, which could easily be impregnated, owing to the superabsorbent acrylic, with an aqueous solution of an active principle.

EXAMPLE 8

Preparation of an impregnated compacted tablet

An impregnated compacted tablet was produced as prepared in Example 5 by replacing the polyamide sold under the trade-name "Nylon 6.6" with the low density polyethylene powder sold under the trade-name "Accurel" already mentioned in Example 6.

An impregnated compacted tablet was obtained having similar properties of those of Example 5.

What we claim is:

1. A process for compacting a powder mixture so as to provide an absorbent or partially friable compacted product, said process comprising placing a quantity of said powder mixture at the bottom of a chamber having a piston slidable therein, causing said piston to slide within said chamber in order to exert a compaction pressure on said powder mixture, said powder mixture containing from 5 to 80% by weight of at least one thermoplastic product having a particle size of between 5 and 500 $\mu$, the remainder being composed of at least one non-thermoplastic product containing a binder and, while exerting said pressure, subjecting said powder mixture to an ultrasonic force.

2. A process according to claim 1, wherein said non-thermoplastic product contains from 0.5 to 20% by weight of a binder.

3. A process according to claim 1, wherein said ultrasound force employed has a frequency ranging from 10 to 100 KHz and an amplitude of from 20 to 6 $\mu$m, the power transmitted to the product during compaction being between 1 and 3 kW/ per cm$^3$ of compact.

4. A process according to claim 1, wherein the duration of emission of said ultrasonic force is between 0.25 and 3.5 seconds.

5. A process according to claim 1, wherein the pressure applied to the powder mixture during ultrasonic emission is between 40 and 200 bars.

6. A process according to claim 1 wherein the powder mixture is placed at the bottom of the compaction chamber in successive layers in which the proportions of thermoplastic and non-thermoplastic powder products are different, the powder mixture layer having the highest content of thermoplastic powder being placed at the bottom of the compaction chamber.

7. A process according to claim 6, wherein two layers are placed at the bottom of the chamber, namely first a layer of thermoplastic product, then layer of non-thermoplastic product.

8. A process according to claim 1, wherein after compaction, the compacted product is filled by immersion in an impregnating fluid.

* * * * *